May 13, 1958 O. R. BRISTOW Plant Pat. 1,703
AZALEA PLANT
Filed May 6, 1957
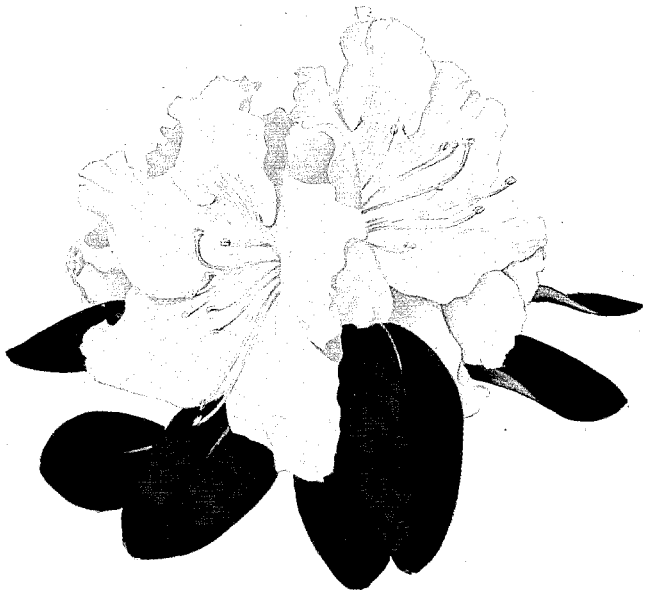
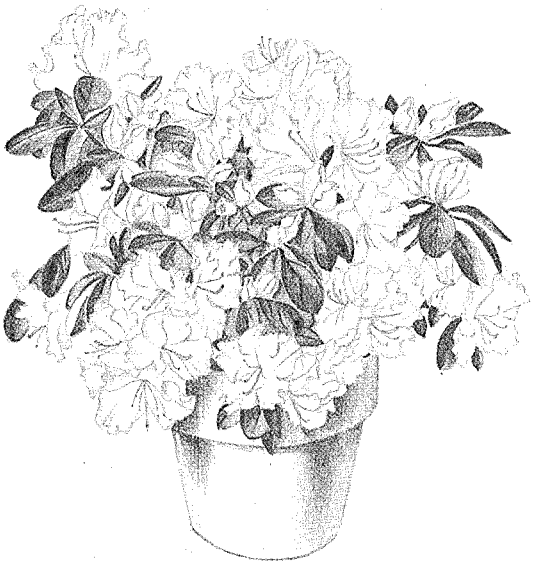
OWEN R. BRISTOW
INVENTOR.
BY Orville R. Seidner
AGENT United States Patent Office Plant Pat. 1,703
Patented May 13, 1958

1,703

AZALEA PLANT

Owen R. Bristow, San Bernardino, Calif., assignor to Mossholder Nursery, Orange County, Calif.

Application May 6, 1957, Serial No. 657,466

1 Claim. (Cl. 47—60)

This invention relates to a distinct and new variety of azalea plant reproduced as a result of deliberate experiments in hybridization carried out at my nursey in San Bernardino, California, the plant being derived from a cross-breeding of unpatented plants numbered 109B and 42 in my breeding records. This particular plant has been given the number 8A for identification purposes.

This distinct and new variety of azalea has an outstanding quality as a forcing plant. In tests conducted, this variety was forced into full bloom, and at that time all the flowers were removed leaving only the buds. Approximately two weeks later this plant came into full bloom again. This re-blooming quality makes the plant an exceptionally valuable commodity for florists and growers.

As a corollary to the aforementioned characteristic, it will be noted that the plant is an exceptionally heavy bud setter with a consequent blooming period of unusually long duration. This characteristic is due to the fact that new flowers continue to open as the older flowers either fall or are removed from the plant.

In addition, the plant is distinguished by its compact growth with little or no trimming or pruning required. A further distinguishing feature is the exceptionally attractive glossy foliage which shows off the plant between the blooming seasons.

It will be noted in the illustration that the bloom of this azalea is an exceptionally fine pastel color having a pinkish-lavender cast, making this plant a valuable Easter forcer for the florists' trade.

Asexual reproduction of this distinct and new variety of azalea was accomplished by me at my nursery in San Bernardino, California, by the known method of removing cuttings from the original hybrid plant which matured from a seedling, and potting the cuttings separately from the donor plant. Subsequent reproductions of the plant in the same manner indicate that the foregoing characteristics as well as further distinguishing characteristics brought forth in the description below are permanently fixed, and the accompanying illustration of a forced cutting grown plant in bloom shows the prolific blooming and the color of the flowers.

The following is a detailed specification of the plant, its foilage, and the flower, reference being had to the British Horticultural Chart of the British Colour Council and to the authority of the Plochere Color System for color identification. The latter system has been originated and published by Gladys and Gustave Plochere of Los Angeles, California, to fill in certain deficiencies of color identification presently inherent in other authorities on color.

*Plant*

Form of plant: Exceptionally bushy and compact; natural bushy grower even when not pruned; symmetrical.
Growth habit: A fast grower.
Rooting: Grows strongly on its own roots; roots well with vigorous roots.

Blooming habit: Exceptionally prolific; 5 to 15 buds on each stem.
Blooming season: Normal heavy blooming season from late March through April; will bloom a few flowers from September to prolific blooming season.
Suitability for forcing: Exceptionally good.

*Foliage*

Size: Leaves average 1¼″ wide and 2¼″ long.
Quantity: Exceptionally heavy.
Color: New foliage—glossy, Plate #1178 on upperside, and flat, Plate #1178 on underside; old foliage—glossy, Plate #1130 on upperside, and Plate #1178 on underside (all Plochere Color System).
Shape: Oval; slightly pointed.
Texture: Normal.
Edge or margin: Normal.
Ribs and veins: Very heavily ribbed and veiny; veins exceptionally prominent on underside.
Aspect: Unusually glossy foliage; foliage very dense.

*Flower*

Size: 3″across flower.
Flowers borne: 5 to 15 on each stem.
Quantity of bloom: Exceptionally abundant.
Continuity: Because of abundant amount of buds, new flowers continue to open as the older flowers fall from the plant; therefore the blooming period is of long duration.
Petalage:
*Size.*—1¼″ wide and 2″ long.
*Number of petals under normal conditions.*—5.
*Color of bud.*—Plochere Plate #486.
*Color of open flower.*—Outside edge of petals, Plochere Plate #486; shading towards center of flower, Plochere Plates #487 and 488. The top petal and one-half of each adjoining petal is white from within ½″ of the tip down to the bottom of the throat and is lightly speckled with the color of British Plate #63/1 (greenish yellow).
*Texture.*—Smooth.
Appearance: Flower is moderately ruffled.
Shape: Single flowers, trumpet shaped.
Arrangement: 5 to 15 on each stem; upright flowers on plant.
Persistence: Exceptionally heavy bud setter.

*Reproductive organs*

Stamens:
*Anther.*—Normal.
*Filament.*—Same color as darkest part of flower (normal).
Pollen: Pale yellow.
Styles: Same color as filament. Stigma.—normal (pale yellow).
Ovary: Normal.

Having illustrated and described the invention or discovery, what is claimed as new and patentable is:

A distinct and new variety of azalea plant, substantially as illustrated and described hereinabove, and characterized generally by its compact bushy growth in the absence of trimming and its attractive green glossy foliage between blooming seasons, and particularly characterized by the exceptional commercial forcing quality as an unusually heavy bud setter with resulting blooming period of longer duration than most known varieties, the flower being characterized by a delicate pastel color particularly suitable for spring and Easter forcing.

No references cited